(12) United States Patent
Jugl et al.

(10) Patent No.: US 9,242,051 B2
(45) Date of Patent: Jan. 26, 2016

(54) NEEDLE ASSEMBLY FOR DRUG DELIVERY DEVICES

(75) Inventors: Michael Jugl, Frankfurt am Main (DE); Axel Teucher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 170 days.

(21) Appl. No.: 13/992,981

(22) PCT Filed: Dec. 8, 2011

(86) PCT No.: PCT/EP2011/072236
§ 371 (c)(1),
(2), (4) Date: Jun. 10, 2013

(87) PCT Pub. No.: WO2012/080086
PCT Pub. Date: Jun. 21, 2012

(65) Prior Publication Data
US 2013/0274679 A1    Oct. 17, 2013

(30) Foreign Application Priority Data
Dec. 13, 2010    (EP) .................................. 10194647

(51) Int. Cl.
*A61M 5/34* (2006.01)
*A61M 5/24* (2006.01)

(52) U.S. Cl.
CPC ............... *A61M 5/345* (2013.01); *A61M 5/347* (2013.01); *A61M 5/348* (2013.01); *A61M 2005/2407* (2013.01); *A61M 2205/6045* (2013.01); *Y10T 29/49815* (2015.01); *Y10T 29/49826* (2015.01)

(58) Field of Classification Search
CPC ....... A61M 5/34; A61M 5/345; A61M 5/347; A61M 5/348; A61M 2205/6045; A61M 2005/2407
USPC ........................................................ 604/201
See application file for complete search history.

(56) References Cited

U.S. PATENT DOCUMENTS

| 2,531,893 | A | | 11/1950 | Roehr |
| 4,973,318 | A | * | 11/1990 | Holm et al. .................... 604/208 |
| 2002/0052579 | A1 | | 5/2002 | Sogaro |
| 2010/0292654 | A1 | * | 11/2010 | Schraga ................ A61M 5/326 604/198 |

* cited by examiner

*Primary Examiner* — Theodore Stigell
*Assistant Examiner* — Amber Stiles
(74) *Attorney, Agent, or Firm* — Fish & Richardson P.C.

(57) ABSTRACT

A needle assembly for a drug delivery device includes a cup-shaped receptacle of non-circular cross-section having a bottom section supporting a needle element. The needle element is adapted to penetrate a pierceable seal of a cartridge to be disposed in a cartridge holder of the drug delivery device. The receptacle includes a fastening mechanism adapted to engage with a fastening mechanism of a support section of the cartridge holder for releasably fastening the needle assembly. The fastening mechanisms are convertible into a release configuration by changing the distance between mutually corresponding fastening mechanisms through twisting the receptacle with respect to the support section.

20 Claims, 3 Drawing Sheets

NEEDLE ASSEMBLY FOR DRUG DELIVERY DEVICES

CROSS REFERENCE TO RELATED APPLICATIONS

The present application is a U.S. National Phase Application pursuant to 35 U.S.C. §371 of International Application No. PCT/EP2011/072236 filed Dec. 8, 2011, which claims priority to European Patent Application No. 10194647.3 filed Dec. 13, 2010. The entire disclosure contents of these applications are herewith incorporated by reference into the present application.

FIELD OF INVENTION

The present invention relates to a drug delivery device and in particular to a needle assembly to be interconnected to a cartridge holding section of a drug delivery device.

BACKGROUND

Drug delivery devices allowing for multiple dosing of a required dosage of a liquid medicament, such as liquid drugs, and further providing administration of the liquid to a patient, are as such well-known in the art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose.

In order to meet these requirements, the number of parts and steps required to assemble the device and an overall number of material types the device is made from have to be kept to a minimum.

Typically, the medicament to be administered is provided in a cartridge that has a moveable piston or bung mechanically interacting with a piston rod of a drive mechanism of the drug delivery device. By applying thrust to the piston in distal direction, a certain amount of the medicinal fluid is expelled from the cartridge.

Drug delivery devices, such like pen-type injectors typically comprise a housing having a cartridge holder for receiving the cartridge filled with the medicament that has to be dispensed. The distal end section of a cartridge holder facing towards the patient during an injector procedure typically comprises a through opening that provides access to a sealed distal end of the cartridge. By way of said through opening, an injection needle or cannula may penetrate the elastic seal to establish a fluid interconnect allowing the medicament to be expelled from the cartridge.

Typically, the disposable injection needle is provided by way of a needle assembly for releasably fastening the injection needle to the cartridge holder. For this purpose, needle assembly and distal end section of the cartridge holder comprise mutually corresponding threads, by way of which the needle assembly is screwed onto the cartridge holder. However, a threaded connection of cartridge holder and needle mount comes along with a number of deficiencies. Such threaded engagement for instance, does not give a perceptible feedback to the user whether needle assembly is securely mounted on the cartridge holder. In practical use, situations may occur, that only a single or a few threads of a cartridge holder and a needle assembly inter-engage, but the needle assembly is not yet securely fastened to the cartridge holder.

A user may then simply not be not aware of such improper and insufficient fastening and may therefore initiate a dose selecting and dispensing procedure. In particular in the course of a dispensing of a dose of the medicament, the needle assembly may autonomously disengage from the cartridge holder, for instance due to a built-up of a fluid pressure and/or when penetrating the skin of the patient. In these cases, the patient would be exposed to an increased health risk.

SUMMARY

It is therefore an object of the present invention, to provide an improved fastening mechanism for a needle assembly and to provide an unambiguous mutual mechanical engagement of cartridge holder and needle assembly. In another object, the invention also aims to provide an easy and user-friendly way of releasably fastening a needle mount to a cartridge holder of a pen-type injection device. It is a further object, to provide a needle assembly mount which is beneficial with respect to production costs and which is particularly suitable for an industrial mass-production process.

The present invention provides a needle assembly for a drug delivery device that comprises a cup-shaped receptacle of non-circular cross section. The cup-shaped receptacle further has a bottom section supporting a needle element. Preferably, the needle element is embedded in the bottom section and is further adapted to penetrate a pierceable seal of a cartridge which is to be positioned in a cartridge holder of a drug delivery device.

The drug delivery device typically comprises a housing and a drive mechanism to be operably engaged with a piston of a cartridge containing the medicament to be dispensed by the device. The housing comprises a cartridge holder or a cartridge holder section and may comprise multiple housing components, such as a main housing component adapted to accommodate the drive mechanism. The cartridge holder or the cartridge holder section is adapted to receive the cartridge.

Irrespective on whether the drug delivery device comprises a single- or multi-component housing, the cartridge holder or cartridge holder section at its distal end is adapted to receive and to support the needle assembly according to the present invention.

The needle element typically comprises a hypodermic needle. With its tipped end facing away from the cartridge, said needle element is adapted to penetrate biological tissue, in particular the skin of a patient for administering of the medicament.

The cup-shaped receptacle further comprises fastening means adapted to engage with corresponding fastening means of a support section of the cartridge holder for releasable fastening the needle assembly to the cartridge holder. Furthermore, the fastening means are convertible into a release configuration by changing the radial distance of mutually corresponding fastening means through twisting the receptacle with respect to the cartridge holder support section. Preferably, the receptacle is twisted with respect to the long axis of the cartridge holder or the drug delivery device. Hence, the central axis of the generally cylindrically shape drug delivery device serves as rotation- or twisting axes in order to engage and/or disengage fastening means of needle assembly and cartridge holder.

Since the cup-shaped receptacle of the needle assembly comprises a non-circular cross section, by twisting the receptacle, radial overlap of mutually corresponding fastening means can be modified such that the fastening means of receptacle and cartridge holder disengage.

Preferably, the receptacle comprises an oval or elliptic cross section. Alternatively, it is also conceivable, that the receptacle is of rectangular or polygonal shape. Additionally, the cup-shaped receptacle can be elastically deformable thereby allowing to modify a relative angle of orientation of cup-shaped receptacle and cartridge holder support section.

In a further aspect, the fastening means of the cartridge holder support section and of the receptacle are adapted to form a positive interlock. Such positive engagement of mutually corresponding fastening means allows for a quick, reliable and releasable fastening of needle assembly and cartridge holder of the drug delivery device.

In a another embodiment, the fastening means of the receptacle comprise two radially inwardly protruding latching elements. By way of the latching elements, a snap-fit interconnect of needle assembly and cartridge holder can be established. In particular, an interconnection of needle assembly and cartridge holder can be generally attained by pushing the cup-shaped receptacle onto the support section of the cartridge holder until the latching elements reach their final assembly configuration. Preferably, accomplishing of a final assembly configuration is accompanied by some perceptible feedback, like an audible or haptic clicking In another embodiment, the latching elements comprise a bevelled face pointing towards a direction of assembly. When assembling needle assembly and cartridge holder, the bevelled face of the latching elements may support temporal elastic deformation of the oval receptacle. Moreover, by way of the bevelled faces, a snap fit of the mutually corresponding latching elements can be attained. In effect, fastening of needle assembly and cartridge holder can be conducted in such a way, that the needle assembly is simply translationally displaced relative to the cartridge holder in proximal direction, i.e. towards the piston of the cartridge even without inducing any twisting or turning motion.

In another independent aspect, the invention further relates to a cartridge holder subassembly for a drug delivery device, wherein the cartridge holder subassembly comprises a cartridge holder adapted to receive a cartridge filled with a medicament to be dispensed by the drug delivery device. A cartridge typically comprises a pierceable seal at a distal end portion and also has an axially displaceable piston at is opposite proximal end portion. Said piston is adapted to become operably engaged with a piston rod of a drive mechanism of the drug delivery device, which is adapted to exert distally directed pressure on said piston for the purpose of expelling a pre-defined dose of the medicinal fluid.

The cartridge holder further comprises a support for a needle assembly, wherein the support features a non-circular cross section.

Furthermore, the cartridge holder or cartridge holder subassembly comprises fastening means adapted to form a positive interlock with corresponding fastening means of the needle assembly. In particular, the cartridge holder subassembly is formed by assembling the needle assembly to the cartridge holder.

The non-circular cross-section of the support section of the cartridge holder preferably corresponds to the geometry and to the non-circular cross section of the cup-shaped receptacle of the needle assembly. Cartridge holder and needle assembly can only be attached and fastened to each other in a preferential direction due to their non-circular cross-section.

Hence, the non-circular cross section prevents mutual fastening of needle assembly and cartridge holder in arbitrary rotative orientations.

Preferably, also the support section of the cartridge holder comprises an oval cross section that corresponds with the cross section of the receptacle of the needle assembly. Preferably, the overall cross-sectional surface of the support section is smaller than the comparable cross-sectional surface of the receptacle. In this way, the distal end of the support section can be at least partially inserted into the receptacle of the needle assembly.

Since receptacle and support section of the cartridge holder comprise substantially corresponding cross sections, depending on their difference with respect to inner and outer diameters and their particular shape of their respective cross sections, a relative twisting of receptacle and support section of the cartridge holder is only possible within a predefined angular range. Geometric design of mutually corresponding fastening elements and the difference in diameter of the support section and the receptacle is chosen in such a way, that the fastening means at least disengage when a maximum allowable relative angle of rotation of support section and receptacle is reached.

According to a further preferred embodiment, the fastening means of the support section comprise at least two radially outwardly protruding elements adapted to engage with corresponding latching elements of the needle assembly. Preferably, the radially outwardly protruding fastening elements of the cartridge holder subassembly only extend within pre-defined margins in circumferential direction. By way of introducing a relative twist of receptacle and support section, mutually engaging fastening elements can be effectively disengaged.

Preferably, the radially outwardly protruding fastening elements of the cartridge holder subassembly comprise a radially extending rib inter-engaging with the radially inwardly protruding latching element of the receptacle of the needle assembly.

In a further preferred embodiment, the latching elements of the cartridge holder are arranged at opposite endpoints of the ovally shaped support section.

In another independent aspect, the invention also relates to a drug delivery device adapted for administering a dose of a medicament. The drug delivery device comprises a housing, a drive mechanism to be operably engaged with a piston of a cartridge for dispensing of a pre-defined dose of a medicament contained in said cartridge. The drug delivery device further comprises a cartridge holder and a respective cartridge displaced therein, which is filled with the medicament to be dispensed. Moreover, the drug delivery device comprises a needle assembly as described above attached or being attachable to the cartridge holder in a way as suggested by the present invention.

In still another aspect, the invention refers to a method of releasably fastening a needle assembly to a cartridge holder of a drug delivery device, wherein the needle assembly comprises a cup-shaped receptacle of non-circular cross section.

The receptacle further has a bottom section supporting or embedding a needle element adapted to pierce a distally located seal of the cartridge. Fastening of the needle assembly to the cartridge holder comprises inserting a distal support section of the cartridge holder of non-circular cross section into the cup-shaped receptacle of non-circular cross section by displacing the receptacle translationally relative to the cartridge holder in axial and proximal direction.

Subsequently, corresponding fastening means of cartridge holder and receptacle are to be mutually engaged by changing the radial distance of the corresponding fastening means by way of twisting the receptacle with respect to the support section, wherein the axis of twisting substantially corresponds to the long axis of the cartridge holder of the drug delivery device.

Furthermore and according to another embodiment, for a disassembly of needle assembly and cartridge holder, the needle assembly is twisted with respect to the cartridge holder for changing the radial distance of the mutually corresponding fastening means, thereby converting the fastening means into a release configuration, which allows to remove the needle assembly from the cartridge holder in distal direction, i.e. by translationally displacing the needle assembly away from the distal support section of the cartridge holder.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the pertinent art, that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be explained in greater detail by making reference to the drawings in which.

DETAILED DESCRIPTION

Figure 1:
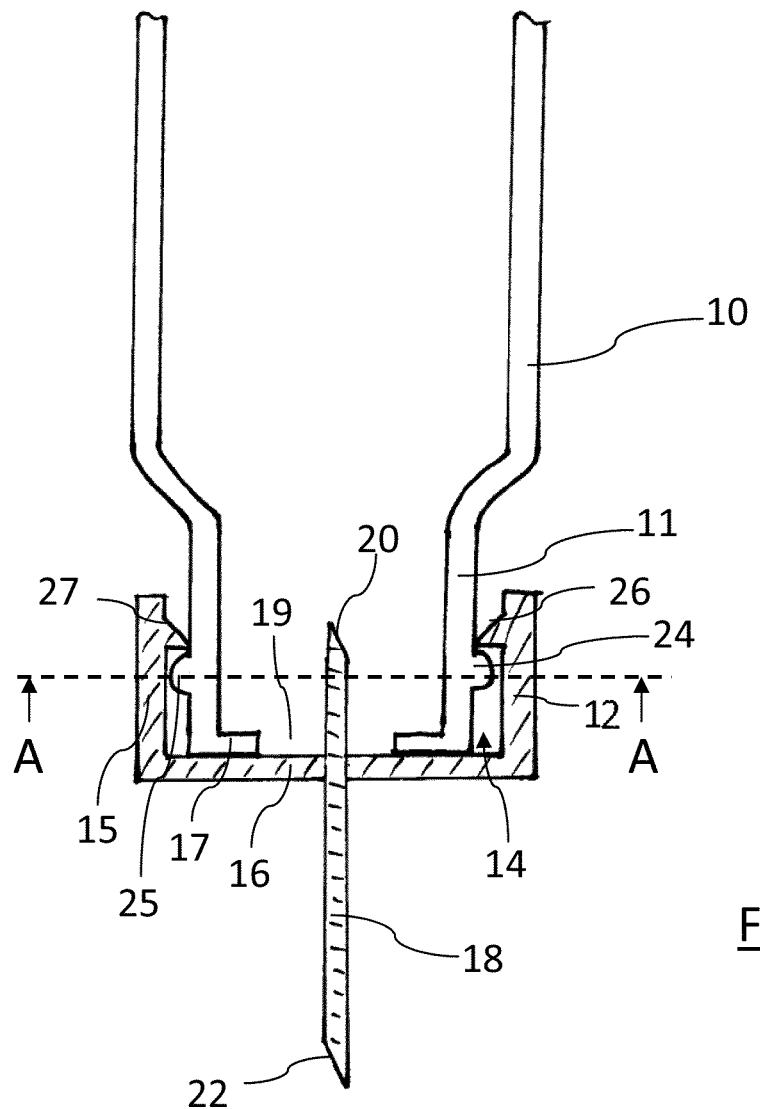
FIG. 1 schematically shows a cartridge holder with a needle assembly attached thereto in a longitudinal cross sectional illustration, FIG. 2 an isolated cross section of the receptacle of the needle assembly along A-A according to FIG. 1, FIG. 3 an isolated cross-sectional illustration of the needle holder along A-A, FIG. 4 the needle assembly according to FIG. 2 and the cartridge holder according to FIG. 3 in final assembly configuration with inter-engaging fastening means, and FIG. 5 the assembly according to FIG. 4 in a twisted and disengaged configuration.

In FIG. 1, a cartridge holder subassembly is illustrated in a longitudinal cross section. The needle assembly 12 substantially comprises a cup-shaped receptacle 14 having a bottom section 16 and a substantially cylindrical and circumferential sidewall 15. In the centre of the bottom section 16, a piercing element, typically in form of an injection needle 18 is embedded having a distal tip 22 and a proximal tip 20. By way of the proximal tip 20, the needle 18 penetrates a pierceable septum of a cartridge, which is not explicitly illustrated here.

The cartridge holder 10 forms part of a housing of the not further illustrated drug delivery device. At its lower, distal section, the cartridge holder 10 comprises a neck portion 11, that serves as support for the cup-shaped receptacle 14.

At its distal end section, the cartridge holder 10 comprises a radially inwardly directed circumferential flange portion 17 abutting with the bottom section 16 of the needle assembly 12. Furthermore, radial extension of the flange 17 defines a through opening 19 for the proximal portion 20 of the needle 18.

As further illustrated in FIG. 1, distal support section 11 of the cartridge holder 10 comprises oppositely disposed and radially extending ribs 24, 25 that are in engagement with radially inwardly protruding latching elements 26, 27 of the sidewall 15 of the receptacle 14.

In the various cross sectional illustrations according to FIGS. 2, 3, 4 and 5, inter-engagement of the fastening means 24, 25, 26, 27 is explained in greater detail.

Figure 2:
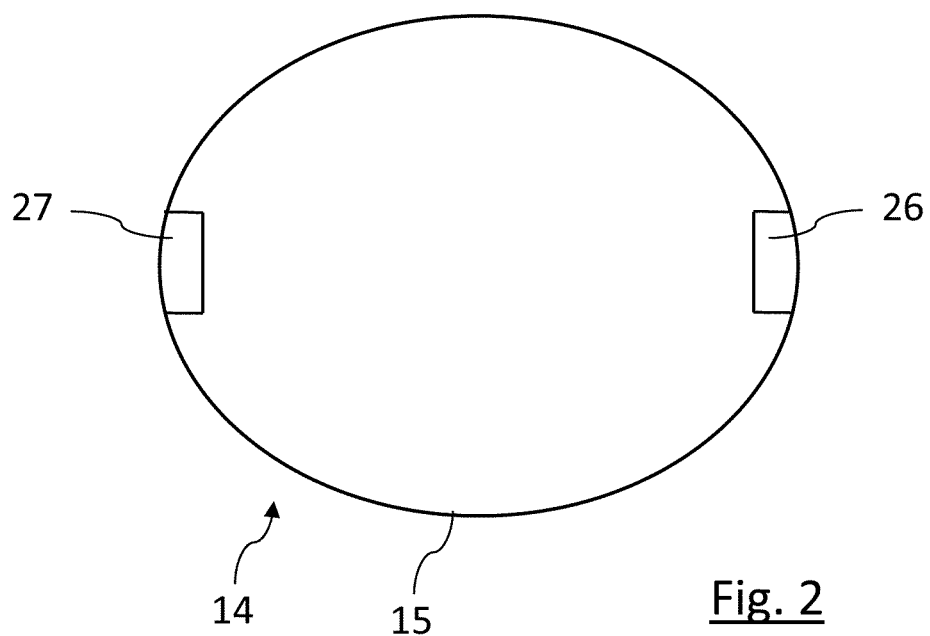
Figure 3:
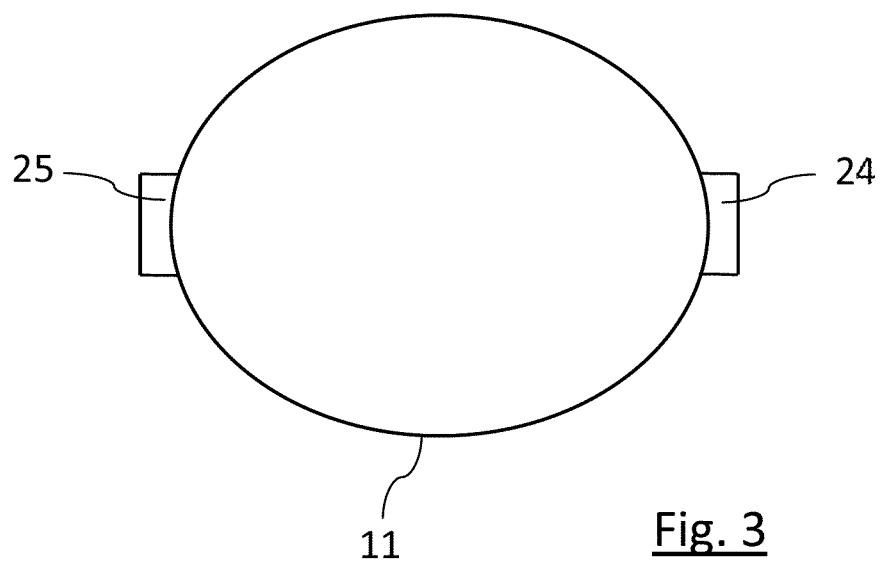

As illustrated in FIGS. 2 and 3, the sidewall 15 of the receptacle 14 is of oval or elliptic shape and comprises radially inwardly protruding snapping or latching elements 26, 27. Correspondingly, the support section 11 of the cartridge holder 10 comprises a respective oval cross section but is smaller in diameter than the receptacle 14. Also, the support section 11 comprises fastening elements 24, 25 in elongation of an imaginary long axis, which is horizontal in FIG. 3.

Mutual distance of protrusions 24, 25 and of protrusions 26, 27 is chosen such, that the mutually corresponding fastening elements 24, 25, 26, 27 overlap in an axial projection when receptacle 14 and support section 11 are arranged in a nested or inter-engaging configuration. The illustrated overlapping of corresponding fastening elements 24, 25, 26, 27 will only be achieved and attained, if the long and short axes of the oval receptacle 14 as well as long and short axes of the support section 11 are oriented substantially parallel to each other. The different radial size of support section 11 and sidewall 15 allows for a relative twisting motion between the receptacle 14 and the support section 11, at least within pre-defined margins.

Figure 4:
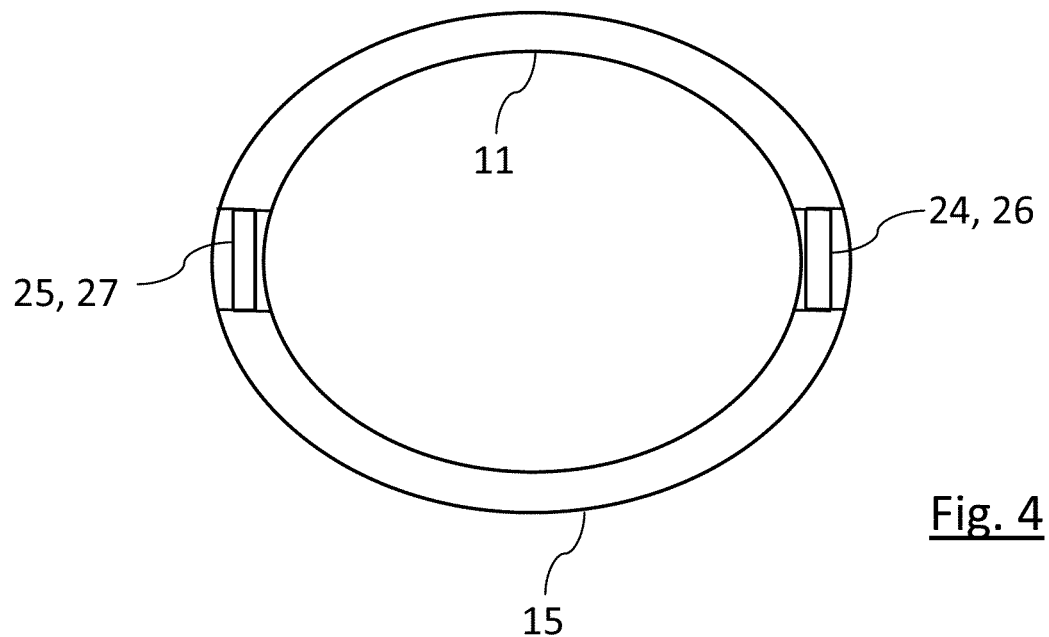
Figure 5:
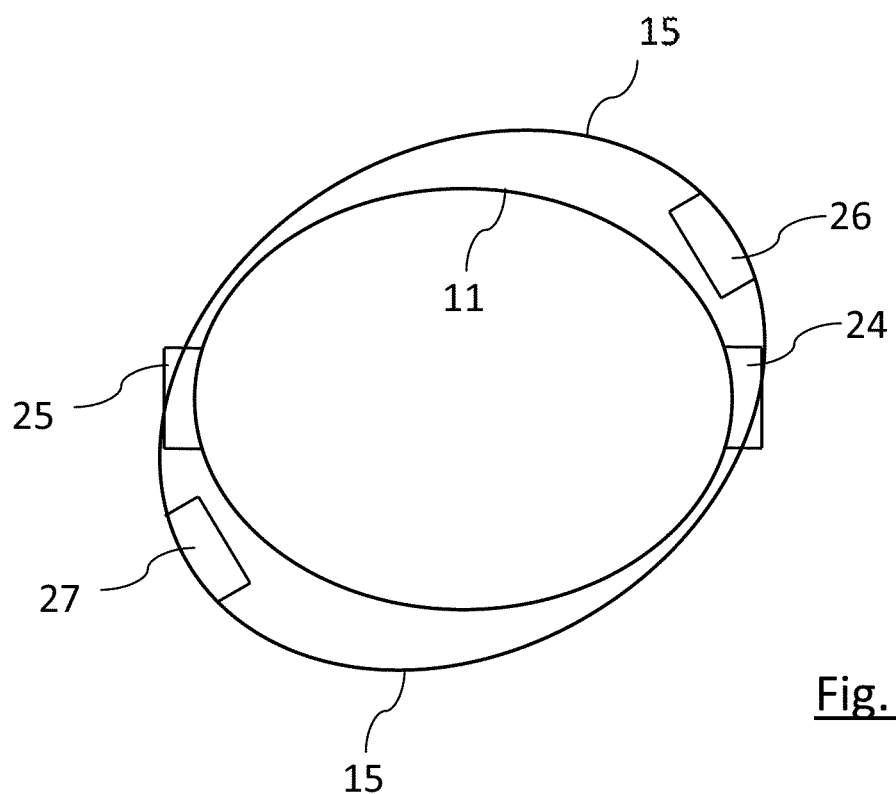

Said margins are chosen in such a way and can be modified by appropriately adapting the overall circumferential geometry of receptacle 14 and support section 11 or by modifying their respective inner or outer diameters. However, by twisting the receptacle 14 counter-clockwise, the configuration as illustrated in FIG. 4 can be converted into a release configuration as shown in FIG. 5.

By way of twisting the receptacle 14 relative to the support section of the cartridge holder, the radial distance of mutually corresponding fastening means is changed in such a way, that the fastening elements 24, 26 and 25, 27 do no longer overlap in an axial projection. Consequently, cartridge holder 10 and needle assembly 12 are no longer positively engaged and the cup-shaped receptacle 14 can be removed from the cartridge holder 10.

The invention claimed is:

1. A needle assembly for a drug delivery device comprising:
a cup-shaped receptacle having a bottom section supporting a needle element being adapted to penetrate a pierceable seal of a cartridge to be disposed in a cartridge holder of the drug delivery device,
wherein the receptacle comprises a sidewall having an oval cross-section, the sidewall comprising two radially inwardly protruding latching elements adapted to engage with two radially outwardly extending ribs of a support section of the cartridge holder for releasably fastening the needle assembly to the cartridge holder, the support section of the cartridge holder comprising an oval cross-section smaller than the receptacle,
wherein the ribs are arranged on opposite endpoints of a long axis of the oval cross-section of the support section, and the latching elements are arranged on opposite endpoints of a long axis of the oval cross-section of the sidewall, and
wherein the latching elements and the ribs are convertible into a release configuration by changing a distance between the latching elements and the ribs through twisting the receptacle with respect to the support section.

2. The needle assembly according to claim 1, wherein the latching elements and the ribs are adapted to form a positive interlock.

3. The needle assembly according to claim 1, wherein the receptacle is elastically deformable.

4. The needle assembly according to claim 1, wherein the latching elements comprise a beveled surface facing towards an insertion direction.

5. A cartridge holder subassembly for a drug delivery device comprising:
a cartridge holder adapted to receive a cartridge filled with a medicament to be dispensed by the drug delivery device, wherein the cartridge comprises a pierceable seal at a distal end portion,
a support section for a needle assembly, the support section comprising an oval cross-section smaller in diameter than a cup-shaped receptacle of the needle assembly, and
two radially outwardly extending ribs adapted to form a positive interlock with and to engage with two radially inwardly protruding latching elements of the needle assembly,
wherein the ribs of the support section are arranged on opposite endpoints of a long axis of the oval cross-section of the support section, and the latching elements of the receptacle are arranged on opposite endpoints of a long axis of an oval cross-section of the receptacle.

6. A drug delivery device for administering a dose of medicament, comprising:
a housing,
a cartridge holder comprising a support section for a needle assembly, the support section comprising an oval cross-section and two radially outwardly extending ribs,
a cartridge received in the cartridge holder and being filled with the medicament,
a drive mechanism to be operably engaged with a piston of the cartridge for dispensing of a pre-defined dose of the medicament, and
a needle assembly for the drug delivery device, the needle assembly comprising:
a cup-shaped receptacle having a bottom section supporting a needle element adapted to penetrate a pierceable seal of the cartridge to be disposed in the cartridge holder of the drug delivery device,
wherein the receptacle comprises a sidewall having an oval cross-section, the sidewall comprising two radially inwardly protruding latching elements adapted to engage with the two radially outwardly extending ribs of the support section of the cartridge holder,
wherein the ribs are arranged on opposite endpoints of a long axis of the oval cross-section of the support section, and the latching elements are arranged on opposite endpoints of a long axis of the oval cross-section of the sidewall, and
wherein the latching elements and ribs are convertible into a release configuration by changing a distance between the latching elements and the ribs through twisting the receptacle with respect to the support section.

7. A method of releasably fastening a needle assembly to a cartridge holder of a drug delivery device, wherein the needle assembly comprises a cup-shaped receptacle comprising an oval cross-section and a bottom section supporting a needle element, wherein fastening of the needle assembly to the cartridge holder comprises:
inserting a distal support section of the cartridge holder comprising an oval cross-section into the cup-shaped receptacle by displacing the receptacle translationally relative to the cartridge holder in a proximal direction; and
after inserting the distal support section of the cartridge holder into the receptacle, twisting the receptacle with respect to the support section to engage radially outwardly protruding ribs of the support section with radially inwardly extending latching elements of the receptacle.

8. The method according to claim 7, further comprising disassembling of the needle assembly and the cartridge holder by twisting the needle assembly with respect to the cartridge holder for changing the distance between the ribs and the latching elements and for converting the ribs into a release configuration.

9. The needle assembly according to claim 1, wherein the support section is configured to be rotatable relative to the receptacle within a margin defined by major and minor diameters of the oval cross-section of the support section and major and minor diameters of the oval cross-section of the sidewall.

10. The needle assembly according to claim 2, wherein the positive interlock comprises an overlap between the latching elements and the ribs in an axial projection.

11. The needle assembly according to claim 10, wherein, in the release configuration, the latching elements and the ribs do not overlap in the axial projection.

12. The cartridge holder subassembly according to claim 5, wherein the support section is configured to be rotatable relative to the receptacle within a margin defined by major and minor diameters of the oval cross-section of the support section and major and minor diameters of the oval cross-section of the receptacle.

13. The cartridge holder subassembly according to claim 5, wherein the positive interlock comprises an overlap between the latching elements and the ribs in an axial projection.

14. The cartridge holder subassembly according to claim 13, wherein:
the latching elements and the ribs are convertible into a release configuration by changing a distance between the latching elements and the ribs through twisting the receptacle with respect to the support section, and the latching elements and the ribs, in the release configuration, do not overlap in the axial projection.

15. The drug delivery device according to claim 6, wherein the latching elements and the ribs are adapted to form a positive interlock, the positive interlock comprising an overlap between the latching elements and the ribs in an axial projection.

16. The drug delivery device according to claim 15, wherein, in the release configuration, the latching elements and the ribs do not overlap in the axial projection.

17. The drug delivery device according to claim 6, wherein the support section is configured to be rotatable relative to the receptacle within a margin defined by major and minor diameters of the oval cross-section of the support section and major and minor diameters of the oval cross-section of the sidewall.

18. The method according to claim 7, wherein the ribs are arranged on opposite endpoints of a long axis of the oval cross-section of the support section, and the latching elements are arranged on opposite endpoints of a long axis of the oval cross-section of the receptacle.

19. The method according to claim 7, wherein twisting the receptacle with respect to the support section comprises twisting the receptacle within a margin defined by major and minor diameters of the oval cross-section of the support section and major and minor diameters of the oval cross-section of the sidewall.

20. The method according to claim 7, wherein twisting the receptacle with respect to the support section comprises twisting the receptacle with respect to the support section such that the latching elements and the ribs form a positive interlock, the positive interlock comprising an overlap between the latching elements and the ribs in an axial projection.

* * * * *